United States Patent

Zhen et al.

[11] Patent Number: 5,817,616
[45] Date of Patent: Oct. 6, 1998

[54] PROCESS FOR PREPARING A FLORAL ODOROUS PERFUME AND PERFUME OBTAINED THEREFORM

[75] Inventors: Liu Zhen; Cheng Zhi; Wang Chang-guo, all of Nanjing, China

[73] Assignees: Nanjing Forestry University; Nanjing Institute for the Comprehensive Utilization of Wild Plants, both of Nanjing, China

[21] Appl. No.: 783,163

[22] Filed: Jan. 14, 1997

[30] Foreign Application Priority Data

Jan. 31, 1996 [CN] China .............................. 96 1 16829.3

[51] Int. Cl.$^6$ ...................................................... A61K 7/46
[52] U.S. Cl. .................................................................. 512/14
[58] Field of Search ............................................ 512/1, 14

[56] References Cited

PUBLICATIONS

Abstract : 509294 "Aromatization Reaction of Longifolene" Liu; Zhen et al. (1992), 12(4) pp. 269–277.

Z. Liu, et al., "Aromatization Reaction of Longifolene," *Chem. & Indus. Forest Prods.*, 12(4):1–12 (1992) (Full English Translation).

Primary Examiner—Terressa Mosley
Attorney, Agent, or Firm—Pennie & Edmonds LLP

[57] ABSTRACT

This invention relates to a process for producing a composition comprising 4,4-dimethyl-6-isopropyl-1,2,3,4-tetrahydronaphthalen-1-one. The composition of the invention is prepared by the oxidation of a 1,1-dimethyl-7-isopropyl -1,2,3,4-tetrahydronaphthalene raw material, which may be prepared by rearrangement and aromatization of longifolene. The invention also relates to perfume comprising the composition of the invention. The process uses organic acid salts of metals, including Cr, Fe, Mn, Ni, and the like, as oxidizing catalysts to produce the compound, which has a floral odor that diffuses easily and is long lasting. The fragrance of 4,4-dimethyl-6-isopropyl-1,2,3,4-tetrahydronaphthalen-1-one is similar to various natural essential oils and their mixtures. Due to both its floral and woody odor, the 4,4-dimethyl-6-isopropyl-1,2,3,4-tetrahydronaphthalen-1-one compound can be advantageously used as an ingredient in various types of perfumery materials.

23 Claims, 3 Drawing Sheets

PROCESS FOR PREPARING A FLORAL ODOROUS PERFUME AND PERFUME OBTAINED THEREFORM

FIELD OF THE INVENTION

This invention relates to a new perfume material and a novel process for preparing thereof.

BACKGROUND OF THE INVENTION

Longifolene is the main component of heavy turpentine oil in Chinese masson's pine, and can be obtained by precise fractionation of heavy turpentine oil or from other natural essential oil. China is rich in pine oleoresin resources. By processing of oleoresin to produce rosin, 8 to 10 thousand tons of heavy turpentine oil can be yielded as side product each year. The heavy turpentine oil is primarily composed of sesquiterpenes such as longifolene, the content of longifolene is in the range of 40 to 65%. Now in China heavy turpentine oil is chiefly used as fuel and solvent except synthesizing a limited number of perfume products in small amount. It has been utilized far from reasonably.

The molecular structure of longifolene is shown in the following:

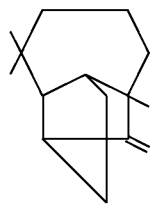

It is a tricyclic sesquiterpene in a high energy state, and can be rearranged into various products in the presence of Lewis acid under different conditions. Under more vigorous condition, longifolene can be rearranged and aromatized into 1,1—dimethyl-7-isopropyl-1,2,3,4-tetrahydronaphthalene having the following structure:

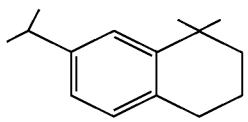

Several catalyst systems have been employed for rearrangement and aromatization of longifolene. such as zinc chloride and zinc chloride—acetic anhydride (Recueil. 1969, 88:313~320), phosphoric acid-silica gel, Amberlyst-15 and boron—trifluoride etherate (J. Indian Chem. Soc., 1978, 1138~1141) and trifluoroacetic acid (chem. & Industry, 1972, 766), etc. 1,1-dimethyl-7-isopropyl-1,2,3,4-tetrahydronaphthalene is an intermediate of potential industrial value. It has a light woody odor with an ambergris note and can be used as perfume fixative in various perfumery compounds. It is mainly employed to synthesize a series of compounds which structures are similar to polycyclic musk and ambergris perfume. These kinds of compounds exist extensively in nature or have been synthesized. Many of them have been commercialized compounds which have similar structures usually possess similar odor characteristic. For example, tetrahydronaphthalen-ones or-ols all have sweet and woody odor with light animal scent. As to fragrant derivatives of 1,1-dimethyl-7-isopropyl-1,2,3,4-tetrahydronaphthalene, D.K. Kettenes studied the odors of the acylated compounds and found that the formylated and acetylated substituted compounds have delicate but weak musk odor. However, up to now no report has been found to describe the existence or synthesis of 4,4-dimethyl-6-isopropyl-1,2,3,4-tetrahydronaphthalen-1-one.

SUMMARY OF THE INVENTION

The object of this invention is to provide a process for preparing a composition comprising a floral odorous compound which is synthesized from 1,1-dimethyl-7-isopropyl-1,2,3,4-tetrahydronaphthalene obtained by rearrangement and aromization of longifolene, and perfume comprising the compound in the composition produced by the process. The chemical name of this new compound is 4,4-dimethyl-6-isopropyl-1,2,3,4-tetrahydronaphthalen-1-one having the following structure:

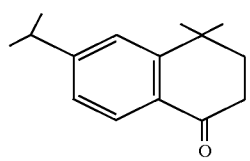

DETAILED DESCRIPTION OF THE INVENTION

First, 1,1-dimethyl-7-isopropyl-1,2,3,4-tetrahydronaphthalene is prepared by rearrangement and aromatization of longifolene, which can be obtained by precise distillation of heavy turpentine oil or other essential oil containing longifolene. Then 4,4-dimethyl-6-isopropyl-1,2,3,4-tetrahydronaphthalen-1-one is synthesized from 1,1-dimethyl-7-isopropyl-1,2,3,4-tetrahydronaphthalene by catalytic oxidation with organic heavy-metal catalyst. The scheme of synthesis is shown in the following:

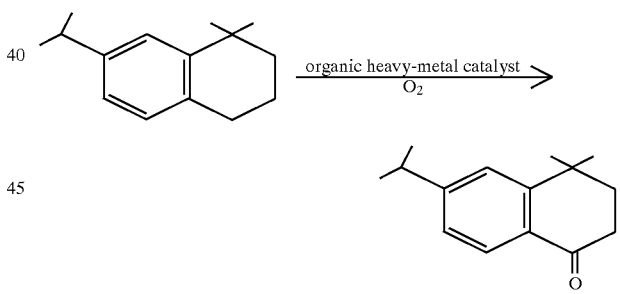

Longifolene raw material may be obtained by precise distillation of heavy turpentine oil or other essential oils, and also commercial products are available in the market. The purity of longifolene usually is in a range of 55 to 75%. The main impurities in the raw material are sesquiterpenes such as carypohyllene.

The purity is measured by GC (GC-9AG, SHIMADZU Co.). The analysis condition is given as follows:

Column: OV-101 fused silica capillary column (Ø0.2mm×25m)

Detector: FID

Carrier gas: $N_2$ ($0.981 \times 10^5 Pa$), $H_2$ ($0.587 \times 10^5 Pa$)

Temperature of vaporization: 230° C.

Temperature of column(programmed temperature): 80° C. to 100° C. (1° C./min), 100° C. to 230° C. (2° C./min)

Temperature of detector: 230° C.
Injecting volume: 0.25µl
Sensitivity: $10^2$
Normalization is used for quantitative analysis.
Peaks are identified by MS (ZAB-HS Mass Spectrometer VG Instruments Group Ltd.)

A Lewis acid combined catalyst is employed for rearrangement and aromatization of longifolene, which contains main catalyst boron-trifluoride etherate and promoter acid anhydrides of low carbon number. Acid anhydrides with low carbon number are acid anhydrides of $C_1$~$C_4$ carboxylic acids, among which acetic anhydride is most commonly used. The amount of acetic anhydride to be used is generally in the range of 0.2 to 10%, preferably 0.5 to 5% the weight of the total longifolene raw material. The amount of main catalyst boron-trifluoride etherate to be used is generally in the range of 1 to 15% . preferably 2 to 10% the weight of the total longifolene raw material. Reaction temperature is generally 90° C. to 180° C., preferably 110° C. to 150° C.

The carbon at the benzylic position of 1,1-dimethyl-7-isopropyl-1,2,3,4-tetrahydronaphthalene which is obtained by rearrangement and aromatization of longifolene is more susceptible to undegraded oxidation to give the corresponding ketone or alcohol. More vigorous oxidation may break the ring to form carboxylic acid. Therefore, in the present invention catalytic oxidation with organic heavy metal catalyst is employed. The organic heavy metal catalysts used in this invention are the organic metal compounds of transition-metals in Group VII B and Group VIII of the Periodic Table, according to CAS nomenclature in which the organic acid salts of metals including Mn, Co, Fe and Ni are the most commonly used, for example, cobalt acetate, cobalt acetylacetonate, cobaltous acetylacetonate, cobalt propionate, cobalt butyrate, cobalt valerate, cobalt caproate, cobalt 2-ethylcaproate, cobalt stearate, cobalt cycloalkanoate, cobalt benzoate, cobalt lactate, iron acetate, iron acetylacetonate, ferrous acetylacetonate, iron lactate, iron propionate, iron butyrate, iron valerate, iron caproate, iron 2-ethylcaproate, iron stearate, iron cycloalkanoate, manganese acetate, nickel acetate, and the other analogous salts. The amount of organic heavy metal catalyst to be used is generally in the range of 0.1 to 30%, preferably 0.2 to 15% the weight of 1,1 -dimethyl-7-isopropyl-1,2,3,4-tetrahydronaphthalene raw material.

In the process for synthesizing 4,4-dimethyl-6-isopropyl-1,2,3,4-tetrahydronaphthalen-1-one by catalytic oxidation of 1,1-dimethyl-7-isopropyl-1,2,3,4-tertrahydronaphthalene with organic heavy metal catalyst, a solvent may be used or not. The solvent to be used is a generally organic polar solvent, such as butanone, ethyl acetate. acetic acid, acetic anhydride, methanol, ethanol, 1-propanol, isopropyl alcohol, n-butyl alcohol, pentanol, hexanol, propyl acetate, butyl acetate, pentyl acetate, ethyl propionate, butyl propionate, pentanone, hexanone, chloroform, dichloroethane, etc.. The solvent to be used can be only one of these above mentioned organic solvents or the mixture of two or more of them. The amount of the organic solvent to be used is generally in the range of about 0.5 to 100 times, preferably 1 to 50 times the weight of 1,1-dimethyl-7-isopropyl-1,2,3,4-tetrahydronaphthalene raw material. The oxidant to be used is generally air, oxygen or other oxygen-containing gases. The oxidant is fed dispersedly and evenly into the reaction system from the bottom of the reactor. The temperature of oxidation reaction is generally from room temperature to 150° C., preferably 40° C. to 120° C.

The said undegraded oxidation of 1,1-7-dimethyl-isopropyl-1,2,3,4-tetrahydronaphthalene may also be accomplished by employing $Cr^{6+}$oxidant in acidic solvent, for example, anhydrous sodium chromate, chromium trioxide, chromium trioxide-pyridine adduct, or tert-butyl chromate etc. The reaction is running in acetic acid and acetic anhydride medium. The reaction temperature is generally 30° C.–70° C., preferably below 50° C. to avoid overoxidation. Compared with catalytic oxidation by air with organic heavy metal catalyst, this process consumes much more oxidant and medium, which are difficult to be recovered and reused. So the product costs higher and a lot of waste liquid is produced. 4,4-dimethyl-6-isopropyl-1,2,3,4-tetrahydronaphthalen-1-one synthesized by 1,1-dimethyl-7-isopropyl-1,2,3,4-tetrahydronaphthalene from industrial longifolene according to the process of this invention may be purified by precise fractionation under reduced pressure, but the product obtained is still a mixture of several sesquiterpene oxides. Except 4,4-dimethyl-6-isopropyl -1,2,3,4-tetrahydronaphthalen-1-one other sesquiterpene oxides are formed from side reactions and from oxidation of other sesquiterpenes in the raw material. The boiling points of these oxides are quite close to that of 4,4-dimethyl-6-isopropyl-1,2,3,4-tetrahydronaphthalen-1-one. If necessary, 4,4-dimethyl-6-isopropyl-1,2,3,4-tetrahydronaphthalen-1-one can be purified by preparing derivatives, for such as semicarbazone, hydrazone etc., or by preparative gas-liquid chromatography. In fact, it is not necessary to separate and purify the product excessively, since this will result in high cost of the product. Actually contribution of each oxides of sesquiterpenes is efficient and necessary to the fragrances of the perfume, same as many natural essential oils having unique odors.

DETAILED DESCRIPTION OF THE PREFERRED EMBODIMENTS OF THE INVENTION

Figure 1:
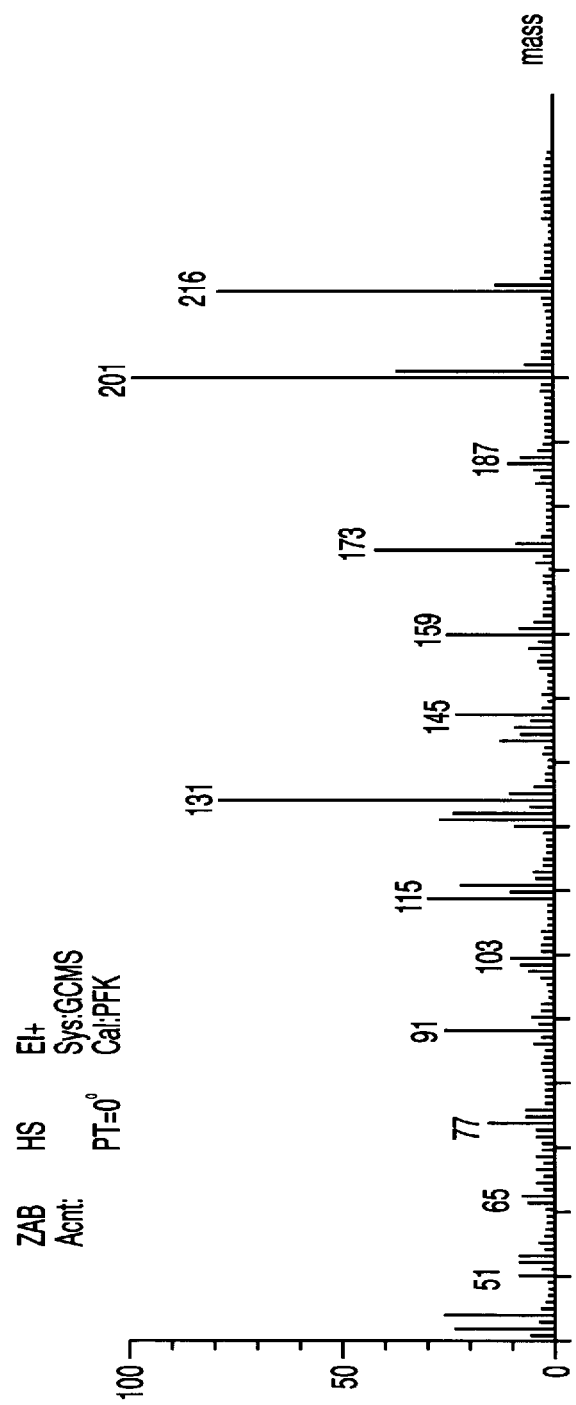
FIG. 1: Mass spectrum of the perfume containing 4,4-dimethyl-6-isopropyl-1,2,3,4-tetrahydronaphthalen-1-one (by ZAB-HS , VG Instrument Group Ltd. U.K.)
Figure 2:
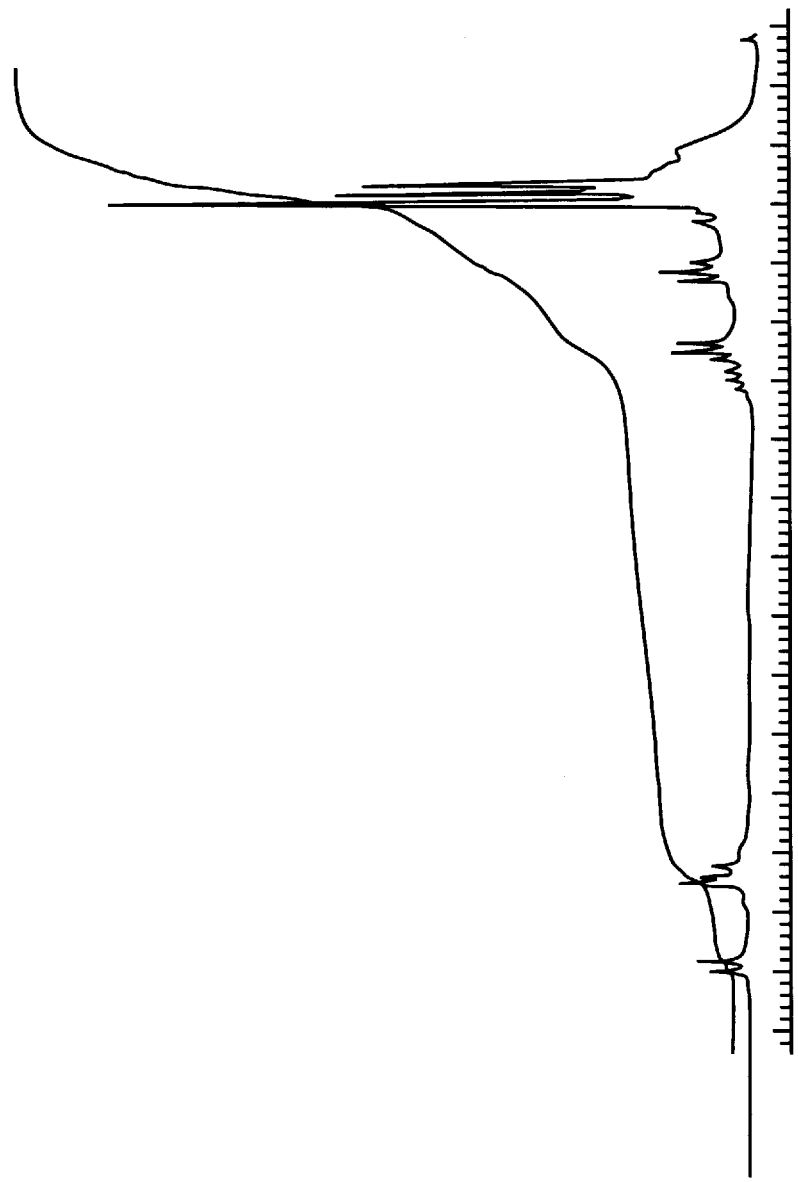
FIG. 2: $^1H$ n.m.r. spectrum of the perfume containing 4,4-dimethyl-6-isopropyl-1,2,3,4-tetrahydronaphthalen-1-one, internal standard: TMS, solvent: $CDCl_3$ (by FX-90Q, JEOL Ltd., JAPAN)
Figure 3:
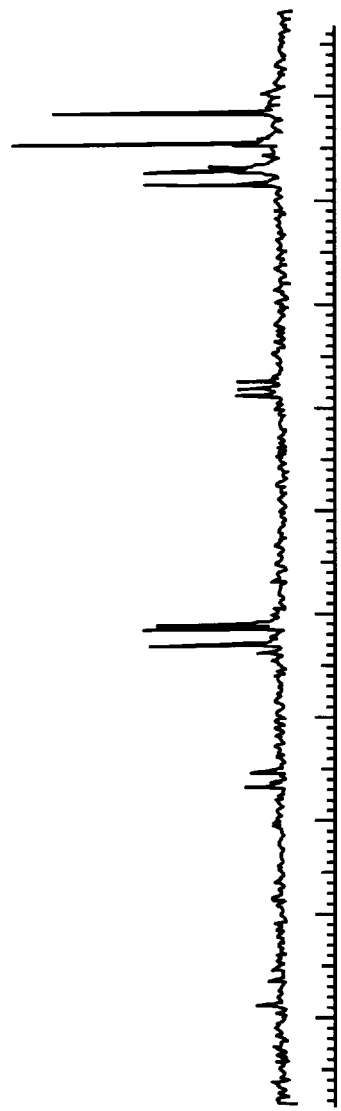
FIG. 3: $^{13}C$ n.m.r. spectrum of the perfume containing 4,4-dimethyl-6-isopropyl-1,2,3,4-tetrahydronaphthalen-1-one. internal standard: TMS, solvent: CDC13 (by FX-90Q, JEOL LTD., JAPAN)

Among the following examples. Example 1 shows a typical process of longifolene rearrangement and aromatization. Example 2 up to Example 8 are typical processes of 1,1 -dimethyl-7-isopropyl-1,2,3,4-tetrahydronaphthalene catalytic oxidation, that is the process for synthesizing 4,4-dimethyl-6-isopropyl-1,2,3,4-tetrahydronaphthalen-1-one. Example 9 gives a detail method to purify 4,4-dimethyl-6-isopropyl-1,2,3,4-tetrahydronaphthalen-1 -one.

EXAMPLE 1

To the mixture of 1224.0 g of commercial longifolene, content of which was 67.2% (measured by GLC), and 32.4 g of acetic anhydride, 46 ml of boron-trifluoride etherate was added gradually in three portions while stirring. The rate of addition was controlled to keep the temperature below 120° C. The mixture was cooled in cold water bath if necessary. After completion of the addition, the mixture was kept stirring for 9 hours at 120° C., then cooled below 100° C., added 800 ml of warm water and stirred for 15 minutes. Next the mixture was stood still for layers separated, and removed water layer. The organic layer was washed with saturated sodium chloride solution to neutral and dried with anhydrous calcium chloride. The product was distillated under reduced pressure. The fraction (b.p.~160° C. under 0.667 kPa) was collected to give 802.5 g of product. The product was analyzed by GC-MS. Longifolene was not found. The product contained 60.1% 1,1-dimethyl-7-isopropyl-1,2,3,4-tetrahydronaphthalene.

EXAMPLE 2

The mixture of 400.0 g of 1,1-dimethyl-7-isopropyl-1,2,3,4-tetrahydronaphthalene (60.1% purity, measured by GLC) and 40.0 g of cobalt acetate was fed with air at 120l/h while vigorous stirring, heated to 50° C. for 36 hours, and then removed solid catalyst by centrifugation to give 482.0 g of liquid crude product. The crude product was distillated under reduced pressure. The fraction (b.p.~190° C. under 1.066 kPa) was collected. About 360.6 g of product was obtained. which contained 40.8% 4,4-dimethyl-6-isopropyl-1,2,3,4-tetrahydronaphthalen-1-one (analyzed by GC). This product was distillated by precise fractionation under reduced pressure. The fraction (b.p. 174°~176° C. under 4.533 kPa) was collected to give 176.0 g of perfume containing 71.9% (measured by GLC) 4,4-dimethyl-6-isopropyl-1,2,3,4-tetrahydronaphthalen-1-one.

EXAMPLE 3

The mixture of 100 g of 1,1-dimethyl-7-isopropyl-1,2,3,4-tetrahydropaphthalene, content of which was 60.1% (measured by GLC), and 10.0 g of manganese acetate was fed with air at 800 ml/min while vigorous stirring, heated to 60° C. for 36 hours, and then removed solid catalyst by centrifugation to give 105.0 g of liquid crude product. The crude product was distillated under reduced pressure. The fraction (b.p. up to 184° C. under 1.066 KPa) was collected. which weighed 69.6 g and contained approximately 38.6% (analyzed by GC) 4,4-dimethyl-6-isopropyl-1,2,3,4-tetrahydronaphthalen-1-one. The fraction was distillated by precise fractionation under reduced pressure at the same condition as that in example 2. the perfume containing 4,4-dimethyl-6-isopropyl-1,2,3,4-tetrahydronaphthalen-1-one was obtained.

EXAMPLE 4

According to the process of Example 3, except that the reaction temperature was 40° C. 73.4 g of crude product was obtained, which contained approximately 21.9% 4,4-dimethyl-6-isopropyl-1,2,3,4-tetrahydronaphthalen-1-one.

EXAMPLE 5

According to the process of example 3, except that the reaction temperature was 110° C. 65.1 g of crude product was obtained, which contained about 37.1% 4,4-dimethyl-6-isopropyl-1,2,3,4-tetrahydronaphthalen-1-one.

EXAMPLE 6

The mixture of 100 g of 1,1-dimethyl-7-isopropyl-1,2,3,4-tetrohydronaphthalene (60.1% purity, measured by GLC), 2.0 g of cobalt acetate and 100 ml of ethyl acetate was fed with air at 800 ml/min while vigorous stirring, heated to 50° C. for 24 hours, then removed solid catalyst by centrifugation and evaporated the solvent to give 115.5 g of liquid crude product. The crude product was distillated under reduced pressure. The fraction (b.p.~186° C. under 1.066kPa) was collected, which weighed 88.0 g and contained about 25.2% (analyzed by GC) 4,4-dimethyl-6-isopropyl-1,2,3,4-tetrahydrenaphthalen-1-one. The fraction was distillated by precise fractionation under reduced pressure at the same condition as that in example 2, the perfume containing 4,4-dimethyl-6-isopropyl-1,2,3,4-tetrahydronaphthalen-1-one was obtained.

EXAMPLE 7

The mixture of 1,1-dimethyl-7-isopropyl-1,2,3,4-tetrahydronaphthalene (60.1% purity, analyzed by GLC) and 1.0 g of one of the four catalysts listed in Table 1 was fed with air at 200 ml/min while vigorous stirring. heated to 60° C. for 24 hours, then cooled, removed catalyst by centrifugation, washed with saturated sodium chloride solution, and dried to give crude product. The crude products were ananlyzed by GC and the results are shown in Table 1.

TABLE 1

Analysis of 4,4-dimethyl-6-isopropyl-1,2,3,4-tetrahydronaphthalen-1-one with different catalysts

| catalyst | product (g) | unreacted 1,1-dimethyl-7-isopropyl-1,2,3,4-tetrahydronaphthalene (%) | 4,4-dimethyl-6-isopropyl-1,2,3,4-tetrahydronaphthalen-1-one (%) |
|---|---|---|---|
| manganese formate | 18.4 | 34.3 | 18.4 |
| nickel acetate | 18.8 | 43.0 | 10.1 |
| iron stearate | 19.8 | 31.6 | 20.1 |
| cobalt stearate | 19.6 | 29.8 | 23.1 |
| none | 20.0 | 54.5 | 0 |

EXAMPLE 8

The mixture of 20.0 g of 1,1-dimethyl-7-isopropyl-1,2,3,4-tetrohydronaphthanlene (60.1% purity, analyzed by GLC), 0.8 g of one of catalysts listed in Table 2 and 20 ml of one of the five solvents listed in Table 2 was fed with air at 200 ml/min of air while vigorous stirring, heated to 50° C. for 24 hours, then cooled, removed catalyst by filtration, washed with saturated sodium chloride solution, dried, and evoporated solvent under reduced pressure to give crude product. The products were analyzed by GC and the results are shown in Table 2.

TABLE 2

Analysis of 4,4-dimethyl-6-isopropyl-1,2,3,4-tetrahydronaphthalen-1-one with different combination of catalyst and solvents

| catalyst | solvent | product (g) | unreacted 1,1-dimethyl-7-isopropyl-1,2,3,4-tetrahydronaphthalene (%) | 4,4-dimethyl-6-isopropyl-1,2,3,4-tetrahydronaphthalen-1-one (%) |
|---|---|---|---|---|
| cobalt acetylacetonate | amyl acetate | 21.9 | 31.1 | 22.7 |
| iron acetylacetonate | ethanol | 21.3 | 35.4 | 18.3 |
| nickel formate | chloroform | 20.9 | 40.6 | 13.2 |

TABLE 2-continued

Analysis of 4,4-dimethyl-6-isopropyl-1,2,3,4-tetrahydronaphthalen-1-one with different combination of catalyst and solvents

| catalyst | solvent | product (g) | unreacted 1,1-dimethyl-7-isopropyl-1,2,3,4-tetrahydronaphthalene (%) | 4,4-dimethyl-6-isopropyl-1,2,3,4-tetrahydronaphthalen-1-one (%) |
|---|---|---|---|---|
| cobalt benzoate | butanone | 21.6 | 31.8 | 21.5 |
| NONE | ethyl acetate | 19.9 | 54.6 | 0 |

EXAMPLE 9

Purification of 4,4-dimethyl-6-isopropyl-1,2,3,4-tetrahydronaphthalen-1-one by semicarbazone:

To 150 ml of anhydrous ethanol, 15.0 g of semicarbazide hydrochloride and 15.0 g of anhydrous sodium acetate were added, heated to boiling and filtrated when the mixture was still hot to obtain filtrate. To the filtrate, 10.0 g of the concetrated fraction obtained by precise fractionation of a crude product under reduced pressure, which contained 71.9% 4,4-dimethyl-6-isopropyl-1,2,3,4-tetrahydronaphthalen-1-one (analyzed by GLC) was added. This mixture was heated in water bath to 60° C. for 1.5 hours, added water until cloudy, and then cooled for crystallizing. The crystal was collected and filtered under reduced pressure to give the crude product. The crude product was recrystallized twice from ethanol and dried to give white crystal 4,4-dimethyl-6-isopropyl-1,2,3,4-tetrahydropaphthalen-1-one semicarbazone (m.p. 205°~206° C.).

In the present invention the perfume containing 4,4-dimethyl-6-isopropyl-1,2,3,4-tetrahydronaphthalen-1-one, as a whole, has a sweet and floral odor with a woody and pollen note during the beginning period, and a heavier woody odor with slight ambergris and musk note during the middle and final periods. The odor of the perfume diffuses well, and retains long. The fragrance of the perfume is similar to many natural essential oils or their mixtures. Due to its both floral and woody odor, the perfume can be extensively used as perfume ingredient in various types of perfumery formulations, and to replace some expensive and rare natural essential oils as perfume ingredients in various blended products, such as floral odorous perfumes, toilet water, spray liquids, soaps, deodorants, detergents (including bath lotions, shampoos, etc.), cosmetics (such as facial milk, sun cream, bath milk), and also in fiber, fiber products and paper products. The amount of the perfume of this invention to be used as a perfume ingredient in a perfumery compand is generally in the range of 0.1 to 15%. preferably 0.5 to 10% of the total amount of the perfumery compound.

In the said process of this invention for synthesizing 4,4-dimethyl-6-isopropyl-1,2,3,4-tetrahydronaphthalen-1-one by undegraded oxidation reaction of 1,1-dimethyl-7-isopropyl-1,2,3,4-tetrahydronaphthalene, although the oxidation may be accomplished by using $Cr^{6+}$compound oxidant in acidic solvent, the process with $Cr^{6+}$oxidant in acidic solvent consumes much more oxidant and medium, which are difficult to be recovered and used, and results in higher cost and a lot of waste liquid compared with the air oxidation method with organic heavy metal catalyst.

What is claimed is:

1. A process for producing a composition comprising 4,4-dimethyl-6-isopropyl-1,2,3,4-tetrahydronaphthalen-1-one, which process comprises oxidizing 1,1-dimethyl-7-isopropyl-1,2,3,4-tetrahydronaphthalene in the presence of oxygen and an organic metal compound comprising at least one transition metal selected from the group consisting of Group VIIB and Group VIII of the Periodic Table, provided that the transition metal is not cobalt, and thereby producing the composition.

2. The process according to claim 1, wherein the organic metal compound comprises an organic acid salt of the transition metal.

3. The process according to claim 1, wherein the transition metal is selected from the group consisting of iron, manganese, and nickel.

4. The process according to claim 1, wherein the organic metal compound is provided in a weight amount of about 0.1% to about 30% of the weight amount of 1,1-dimethyl-7-isopropyl-1,2,3,4-tetrahydronaphthalene.

5. The process according to claim 4, wherein the organic metal compound is provided in a weight amount of about 0.2% to about 15% of the weight amount of 1,1-dimethyl-7-isopropyl-1,2,3,4-tetrahydronaphthalene.

6. The process according to claim 1, wherein the oxidation of 1,1-dimethyl-7-isopropyl-1,2,3,4-tetrahydronaphthalene is in the presence of also an organic polar solvent selected from the group consisting of butanone, ethyl acetate, pentyl acetate, acetic anhydride, acetic acid, ethanol, chloroform, and a mixture of two or more thereof.

7. The process according to claim 6, wherein the organic polar solvent is provided in a weight amount about 0.5 to about 100-fold the weight amount of 1,1-dimethyl-7-isopropyl-1,2,3,4-tetrahydronaphthalene.

8. The process according to claim 7, wherein the organic polar solvent is provided in a weight amount of about 1 to about 50-fold the weight amount of 1,1-dimethyl-7-isopropyl-1,2,3,4-tetrahydronaphthalene.

9. The process according to claim 1, wherein the temperature for the oxidation reaction is between about room temperature to about 150° C.

10. The process according to claim 9, wherein the temperature for the oxidation reaction is between about 40° C. to about 120° C.

11. A process for producing a composition comprising 4,4-dimethyl-6-isopropyl-1,2,3,4-tetrahydronaphthalen-1-one, which process comprises oxidizing 1,1-dimethyl-7-isopropyl-1,2,3,4-tetrahydronaphthalene in the presence of oxygen and an organic acid salt selected from the group consisting of cobalt acetate, cobalt acetylacetonate, cobaltous acetylacetonate, cobalt propionate, cobalt butyrate, cobalt valerate, cobalt caproate, cobalt 2-ethylcaproate, cobalt stearate, cobalt cycloalkanoate, cobalt benzoate, cobalt lactate, iron acetate, iron acetylacetonate, ferrous acetylacetonate, iron lactate, iron propionate, iron butyrate, iron valerate, iron caproate, iron 2-ethylcaproate, iron stearate, iron cycloalkanoate, manganese acetate and nickel acetate, and thereby producing the composition.

12. A perfume comprising 4,4-dimethyl-6-isopropyl-1,2,3,4-tetrahydronaphthalene-1-one in the composition produced by the process according to claim 11.

13. A process for producing a composition comprising 4,4-dimethyl-6-isopropyl-1,2,3,4-tetrahydronaphthalen-1-one, which process comprises:

rearranging and aromatizing longifolene to produce 1,1-dimethyl-7-isopropyl-1,2,3,4-tetrahydronaphthalene;

oxidizing 1,1-dimethyl-7-isopropyl-1,2,3,4-tetrahydronaphthalene to produce 4,4-dimethyl-6-isopropyl -1,2,3,4-tetrahydronaphthalen-1-one; and thereby producing the composition; wherein the rearrangement and aromatization of longifolene is catalyzed by a mixture comprising boron-trifluoride etherate and an acid anhydride.

14. The process according to claim 13, wherein the acid anhydride of low carbon number is a $C_1$ to $C_4$ carboxylic acid.

15. The process according to claim 13, wherein the acid anhydride of low carbon number is acetic anhydride.

16. The process according to claim 15, wherein the acetic anhydride is provided in a weight amount of about 0.2% to about 10% of the weight amount of longifolene.

17. The process according to claim 16, wherein the acetic anhydride is provided in a weight amount of about 0.5% to about 5% of the weight amount of longifolene.

18. The process according to claim 13, wherein the boron-trifluoride etherate is provided in a weight amount of about 1% to about 15% of the weight amount of longifolene.

19. The process according to claim 18, wherein said boron-trifluoride etherate is provided in a weight amount of about 2% to about 10% of the weight amount of longifolene.

20. The process according to claim 13, wherein the rearrangement and aromatization of longifolene is carried out at a temperature between about 90° C. to about 180° C.

21. The process according to claim 20, wherein the rearrangement and aromatization of longifolene is carried out at a temperature between about 110° C. to about 150° C.

22. A perfume comprising 4,4-dimethyl-6-isopropyl-1,2,3,4-tetrahydronaphthalene-1-one in the composition produced by the process according to claim 13.

23. A perfume comprising 4,4-dimethyl-6-isopropyl-1,2,3,4-tetrahydronaphthalene-1-one in the composition produced by the process according to claim 1.

* * * * *